US012668565B2

(12) United States Patent
Jung et al.

(10) Patent No.: US 12,668,565 B2
(45) Date of Patent: Jun. 30, 2026

(54) PROCESS FOR HYDROGENATION OF PHTHALATE COMPOUND

(71) Applicant: HANWHA SOLUTIONS CORPORATION, Seoul (KR)

(72) Inventors: Kitaeg Jung, Daejeon (KR); Hyo Suk Kim, Daejeon (KR); Seongmin Park, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 501 days.

(21) Appl. No.: 18/258,574

(22) PCT Filed: Dec. 10, 2021

(86) PCT No.: PCT/KR2021/018814
§ 371 (c)(1),
(2) Date: Jun. 21, 2023

(87) PCT Pub. No.: WO2022/139288
PCT Pub. Date: Jun. 30, 2022

(65) Prior Publication Data
US 2024/0034713 A1 Feb. 1, 2024

(30) Foreign Application Priority Data
Dec. 23, 2020 (KR) ........................ 10-2020-0182598

(51) Int. Cl.
*C07C 67/303* (2006.01)
*C07C 67/58* (2006.01)

(52) U.S. Cl.
CPC ............ *C07C 67/303* (2013.01); *C07C 67/58* (2013.01)

(58) Field of Classification Search
CPC ... C07C 67/303; C07C 67/58; C07C 2601/14; C07C 29/78; C07C 67/54; C07C 29/149; C07C 67/56; C07C 67/60; C07C 69/75
See application file for complete search history.

(56) References Cited

U.S. PATENT DOCUMENTS

| | | | |
|---|---|---|---|
| 2020/0283369 | A1 | 9/2020 | Jung |
| 2020/0361846 | A1 | 11/2020 | Kim |

FOREIGN PATENT DOCUMENTS

| | | | | | |
|---|---|---|---|---|---|
| CN | 105384599 | A | | 3/2016 | |
| CN | 106518608 | A | * | 3/2017 | ........... C07C 29/149 |
| CN | 108940305 | A | | 12/2018 | |
| CN | 210560278 | U | | 5/2020 | |
| CN | 111406044 | A | | 7/2020 | |
| GB | 879264 | A | | 10/1961 | |
| JP | S47-003110 | A | | 2/1972 | |
| JP | 2016-539106 | A | | 12/2016 | |
| JP | 2018-504268 | A | | 2/2018 | |
| JP | 2020-124663 | A | | 8/2020 | |

(Continued)

OTHER PUBLICATIONS

International Search Report Dated Mar. 18, 2022.

*Primary Examiner* — Deborah D Carr
(74) *Attorney, Agent, or Firm* — Harvest IP Law, LLP

(57) ABSTRACT

Provided is a hydrogenation method of a phthalate-based compound. According to the present invention, after hydrogenation of the phthalate-based compound, a reaction product is stably decompressed to separate and recover unreacted hydrogen, thereby improving stability and economic efficiency of the process.

8 Claims, 1 Drawing Sheet

(56) References Cited

FOREIGN PATENT DOCUMENTS

| | | | |
|---|---|---|---|
| JP | 2021-511287 | A | 5/2021 |
| JP | 2021-511288 | A | 5/2021 |
| KR | 2009-0122634 | A | 12/2009 |
| KR | 10-2015-0072197 | A | 6/2015 |
| KR | 10-1556340 | B1 | 9/2015 |
| KR | 2016-0143620 | A | 12/2016 |
| KR | 2017-0025052 | A | 3/2017 |
| KR | 10-2019-0063104 | A | 6/2019 |
| KR | 10-2019-0063105 | A | 6/2019 |
| KR | 10-2019-0063106 | A | 6/2019 |

* cited by examiner

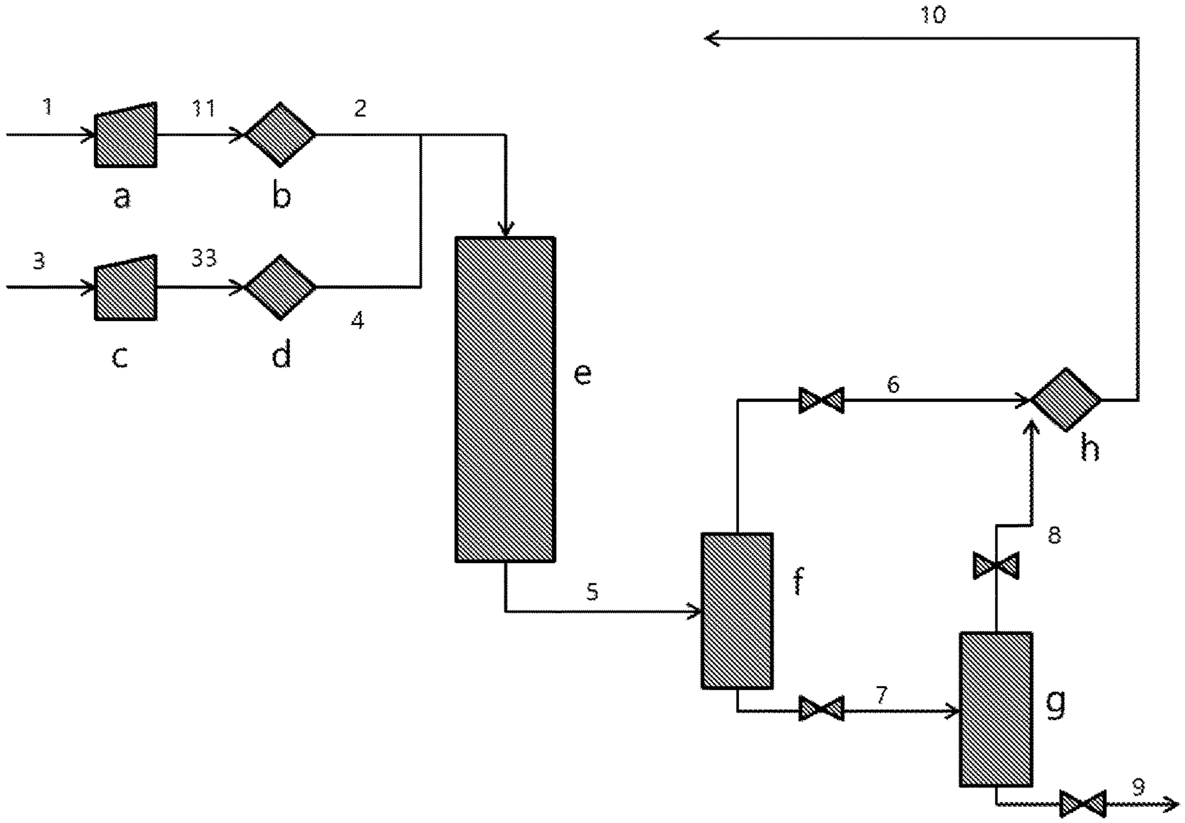
10
1
11
2
a
b
3
33
c
d
4
e
6
h
8
5
f
7
g
9

PROCESS FOR HYDROGENATION OF PHTHALATE COMPOUND

CROSS-REFERENCE TO RELATED APPLICATION

This application is a National Stage International Application PCT/KR2021/018814 filed on Dec. 10, 2021, claiming based on Korean Patent Application No. 10-2020-0182598, filed on Dec. 23, 2020, the disclosure of which is hereby incorporated by reference herein in its entirety.

TECHNICAL FIELD

The present invention relates to a method of stably separating unreacted hydrogen which is included in a reaction product of a high-temperature/high-pressure hydrogenation reaction of a phthalate-based compound.

BACKGROUND ART

A phthalate-based compound is a material widely used as a plasticizer of plastic, particularly, polyvinylchloride (PVC). For example, it is used for various applications such as electrical and electronic products, medicines, paints, lubricants, binders, surfactants, adhesives, tiles, food containers, packaging materials, etc.

However, several phthalate-based compounds are known as materials to cause environmental pollution and endocrine disruption of human, and the regulation of utilization is being strengthened around advanced countries such as Europe, the US, etc. Particularly, among the phthalate-based plasticizers, some products such as di(2-ethylhexyl) phthalate (DEHP), butyl benzyl phthalate (BBP), or di-n-butyl phthalate (DBP) are suspected as environmental hormones which are endocrine disruptors that disturb or confuse the hormone action of human, and therefore, there is a move for the regulation of the same.

Accordingly, efforts are being made to develop environmentally friendly plasticizers that exhibit equivalent performance to the existing plasticizers while being free from environmental hormone issues, and one of them is a method of using a compound in which a benzene ring included in a phthalate compound is hydrogenated. As the hydrogenation of an aromatic compound such as a benzene ring, a method of using a catalyst including a transition metal such as ruthenium as an active ingredient on a carrier is known.

On the other hand, after the hydrogenation reaction process, unreacted hydrogen that does not react with raw materials and hydrogen dissolved in a high-temperature/high-pressure mixture exist. When hydrogen is present in a reaction product, it promotes production of by-products and interferes with production of desired phthalate-based compounds. In addition, from the viewpoint of economic efficiency, it is preferable that unreacted hydrogen is reused by recycling it to a reactor after separation. However, since the hydrogenation reaction of phthalate-based compounds is performed at high temperature/high pressure, studies are needed to stably separate hydrogen from the high-temperature/high-pressure reaction product.

DISCLOSURE

Technical Problem

There is provided a hydrogenation method of a phthalate-based compound, the method inhibiting loss of hydrogen and a target product by stably decompressing hydrogen from a reaction product after a high-temperature/high-pressure hydrogenation reaction of a phthalate-based compound.

Technical Solution

There is provided a hydrogenation method of a phthalate-based compound, the method including the step of injecting, into a reactor, a gas-phase raw material including hydrogen and a liquid-phase raw material including the phthalate-based compound, and the step of performing a hydrogenation reaction of the gas-phase raw material and the liquid-phase raw material in the presence of a catalyst in the reactor, a first decompression step of separating and decompressing, in a first gas-liquid separator, a first solution and the gas-phase material containing hydrogen from the reaction product after the reaction step, and a second decompression step of separating and decompressing, in a second gas-liquid separator, a second solution and the gas-phase material containing hydrogen from the first solution discharged from the lower part of the first gas-liquid separator.

As used herein, the terms “the first”, “the second”, and the like are used to describe a variety of components, and these terms are merely employed to differentiate a certain component from other components.

Further, the terms used in this description are just for explaining exemplary embodiments and it is not intended to restrict the present invention.

The singular expression may include the plural expression unless it is differently expressed contextually.

It must be understood that the term “include”, “equip”, or “have” in the present description is only used for designating the existence of characteristics taken effect, numbers, steps, components, or combinations thereof, and do not exclude the existence or the possibility of addition of one or more different characteristics, numbers, steps, components or combinations thereof beforehand.

The present invention may be variously modified and have various forms, and specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

As used herein, the “gas-phase raw material”, which is a gas-phase material supplied to the reactor, includes hydrogen, and the “liquid-phase raw material” includes phthalate-based compounds, alcohols, cyclohexane-based compounds, etc. In addition, the “reaction product” includes hydrogenated phthalate-based compounds and unreacted gas-phase raw materials including hydrogen, which are discharged from the reactor, etc.

As used herein, the “operating pressure” of the gas-liquid separator includes the pressure of the gas-phase material or solution connected to the upper part and the lower part of the gas-liquid separator. In addition, the pressure of the gas-phase material or solution “discharged” from the upper or lower part of the gas-liquid separator means the decompressed pressure of the gas-phase material or solution connected to the gas-liquid separator by a valve, etc.

Hereinafter, the present invention will be described in detail.

Provided is a method of a hydrogenation method of a phthalate-based compound, the method including the step of injecting, into a reactor, a gas-phase raw material including hydrogen and a liquid-phase raw material including the phthalate-based compound, and the step of performing a hydrogenation reaction of the gas-phase raw material and the liquid-phase raw material in the presence of a catalyst in the reactor, a first decompression step of separating and decompressing, in a first gas-liquid separator, a first solution and the gas-phase material containing hydrogen from the reaction product after the reaction step, and a second decompression step of separating and decompressing, in a second gas-liquid separator, a second solution and the gas-phase material containing hydrogen from the first solution discharged from the lower part of the first gas-liquid separator.

The hydrogenation reaction of the phthalate-based compound according to the present invention is performed by the reaction of the liquid-phase raw material including the phthalate-based compound and the gas-phase raw material including hydrogen. The phthalate-based compound may be specifically a phthalate compound represented by the following Chemical Formula 1, a terephthalate compound represented by the following Chemical Formula 2, an isophthalate compound represented by the following Chemical Formula 3, and carboxylic acid derivatives thereof, or a mixture thereof.

[Chemical Formula 1]

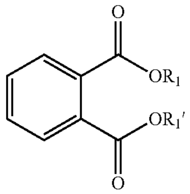

[Chemical Formula 2]

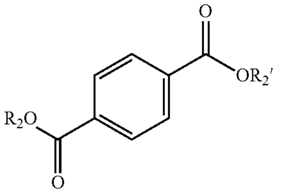

[Chemical Formula 3]

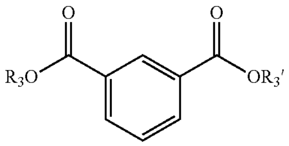

In Chemical Formulae 1 to 3, $R_1$, $R_1'$, $R_2$, $R_2'$, $R_3$, and $R_3'$ may be the same as or different from each other, and each independently selected from hydrogen or a straight or branched alkyl group having 1 to 20 carbon atoms, preferably, 4 to 20 carbon atoms.

Specific examples of the phthalate-based compounds represented by Chemical Formulae 1 to 3 may include dibutyl phthalate (DBP), dihexyl phthalate (DHP), dioctyl phthalate (DOP), di-n-octyl phthalate (DnOP), diisononyl phthalate, or diisodecyl phthalate (DIDP), dibutyl terephthalate (DBTP), dioctyl terephthalate (DOTP), diisononyl terephthalate (DINTP), diisodecyl terephthalate (DIDTP), dibutyl isophthalalate (DBIP), dioctyl isophthalate (DOIP), diisononyl isophthalate (DINIP), or diisodecyl isophthalate (DIDIP), etc., and mixtures thereof.

With regard to the hydrogenation reaction of the phthalate-based compound according to the present invention, the liquid-phase raw material may further include alcohol or hydrogenated phthalate-based compound, etc. The hydrogenated phthalate-based compound may be a cyclohexane-based compound. In addition, when alcohol is included in the liquid-phase raw material, solubility of hydrogen is increased, and thus the hydrogenation reaction is improved, and the lifetime of the catalyst may be improved.

With regard to the hydrogenation reaction of the phthalate-based compound according to the present invention, the gas-phase raw material includes hydrogen. The pressure of hydrogen supplied to the reactor is 100 barg to 200 barg, preferably, 120 barg to 170 barg. In addition, the amount of hydrogen introduced into the reactor is 3 moles to 10 moles, preferably, 3 moles to 6 moles with respect to 1 mole of the phthalate-based compound.

The hydrogenation reaction of the phthalate-based compound according to the present invention is a reaction of the liquid-phase raw material with hydrogen included in the gas-phase raw material. In this regard, the operating temperature of the reactor where the hydrogenation reaction occurs may be 100° C. to 300° C., preferably, 120° ° C. to 250° C. When the reaction temperature is lower than 100° C., the reaction rate is too slow and the reaction may not smoothly occur, and when the reaction temperature is higher than 300° ° C., by-products rapidly increase, which may significantly increase the acid value of the product and may adversely affect the lifetime of the catalyst.

Further, the operating pressure of the reactor may be 100 barg to 200 barg, preferably, 120 barg to 170 barg. When the reaction pressure is lower than 100 barg, the reaction may not occur, and when the reaction pressure is higher than 200 barg, there may be problems of excessive power consumption and a significant increase in manufacturing costs for equipment such as a reactor, etc.

Further, in the hydrogenation method of the phthalate-based compound according to an embodiment of the present invention, the hydrogenation reaction is performed in the presence of a hydrogenation catalyst.

The hydrogenation catalyst may include a transition metal as an active ingredient, preferably, one or more selected from the group consisting of ruthenium (Ru), palladium (Pd), rhodium (Rh) and platinum (Pt).

This hydrogenation catalyst may be used after being supported on a carrier, and in this regard, a carrier known in the art may be used without limitation. Specifically, one or more carriers such as zirconia ($ZrO_2$), titania ($TiO_2$), alumina ($Al_2O_3$), silica ($SiO_2$), etc. may be used.

The active ingredient of the hydrogenation catalyst may be included in an amount of 0.3 parts by weight to 5 parts by weight with respect to 100 parts by weight of the carrier.

By the hydrogenation reaction, the aromatic ring in the phthalate-based compound is hydrogenated and converted to the corresponding compound.

Further, the hydrogenation method of the phthalate-based compound according to the present invention includes a first decompression step performed in a first gas-liquid separator and a second decompression step performed in a second gas-liquid separator, after the reaction step of the phthalate-based compound.

According to one embodiment of the present invention, the reaction product discharged from the reactor may be directly connected to the first gas-liquid separator. Here, the meaning of being directly connected is that the stream discharged from the reactor is directly injected into the first gas-liquid separator without undergoing separate heat exchange or compression, etc. For example, the reaction product injected into the first gas-liquid separator may be directly injected into the gas-liquid separator without cooling. When the reaction product injected into the gas-liquid separator is cooled, solubility of unreacted hydrogen increases, and thus it is difficult to separate and discharge hydrogen from the gas-liquid separator, and the process conditions become harsh. In addition, as the reaction product is injected into the gas-liquid separator without the separate cooling step, there are advantages in that energy efficiency may be increased and dissolved hydrogen may be recovered.

The first decompression step through the first gas-liquid separator is a step of separating and discharging the first solution and hydrogen by injecting the reaction product discharged from the reactor into the first gas-liquid separator. The reaction product that has passed through the reactor may include hydrogenated phthalate-based compound, unreacted phthalate-based compound, unreacted hydrogen, alcohol, etc.

In the first decompression step performed in the first gas-liquid separator, specifically, the gas-phase material including hydrogen is discharged from the upper part of the first gas-liquid separator, and the first solution including the hydrogenated phthalate-based compound, dissolved hydrogen, etc. is discharged from the lower part. In addition, the gas-phase material may include hydrogen, evaporated hydrogenated or unhydrogenated phthalate-based compound, evaporated alcohol, etc., and the first solution may include hydrogenated phthalate-based compound, unreacted phthalate-based compound, alcohol, dissolved hydrogen, etc.

According to one embodiment of the present invention, the operating pressure of the first gas-liquid separator may be 100 barg to 200 barg, preferably, 120 barg to 170 barg. When the operating pressure is lower than 100 barg, there may be a problem in that by-products rapidly increase, and when the operating pressure is higher than 200 barg, there may be a problem in that it is difficult to manufacture a commercial-scale facility, or equipment costs rapidly increase.

The pressure of the gas-phase material discharged from the upper part of the first gas-liquid separator may be 5 barg to 50 barg, preferably, 20 barg to 30 barg. When the pressure of the discharged gas-phase material is lower than 5 barg, additional facilities, such as a compressor, etc., for recovering and recycling the discharged hydrogen are required in order to prevent hydrogen loss. When the pressure is higher than 50 barg, there may be a problem in the operation of the separation/purification process when there is no additional decompression equipment.

The hydrogenation method of the phthalate-based compound according to the present invention includes the step of additionally separating dissolved hydrogen and gas-phase unreacted materials included in the first solution by injecting the first solution which is discharged from the lower part of the first gas-liquid separator, that is, which is subjected to decompression, into the second gas-liquid separator.

The gas-phase material including hydrogen is discharged from the upper part of the second gas-liquid separator, and the second solution including the hydrogenated phthalate-based compound is discharged from the lower part thereof. In addition, the gas-phase material may include hydrogen, evaporated hydrogenated or unhydrogenated phthalate-based compound, evaporated alcohol, etc., and the second solution may include hydrogenated phthalate-based compound, unreacted phthalate-based compound, alcohol, dissolved hydrogen, etc.

The operating pressure of the second gas-liquid separator may be 5 barg to 100 barg, preferably, 20 barg to 30 barg. When the operating pressure of the second gas-liquid separator is lower than 5 barg, there may be a problem of recovering hydrogen discharged in a gas phase by installing a hydrogen compressor, etc. When the operating pressure is higher than 100 barg, the investment cost for hydrogen separation equipment increases, a large amount of hydrogen is included in the raw material discharged in a liquid phase, which may cause hydrogen loss and safety problems due to discharge of hydrogen.

The pressure of the gas-phase material discharged from the upper part of the second gas-liquid separator may be 5 barg to 50 barg, preferably, 20 barg to 30 barg. When the pressure of the discharged gas-phase material is lower than 5 barg, additional facilities, such as a compressor, etc., for recovering and recycling the discharged hydrogen are required in order to prevent hydrogen loss. When the pressure is higher than 50 barg, there may be a problem in the operation of the separation/purification process when there is no additional decompression equipment.

The pressure of the second solution discharged from the lower part of the second gas-liquid separator may be −1 barg to 25 barg, preferably, −0.95 barg to 10 barg. When the discharge pressure is lower than −1 barg, there may be a problem in that process cost increases due to excessive decompression. When the discharge pressure is higher than 25 barg, the equipment investment cost for the subsequent separation vessel increases, additional facilities are required to recover hydrogen and some alcohol in the gas-phase raw material, and there may be safety problems during commercial operation.

In addition, the hydrogen concentration in the second solution discharged from the lower part of the second gas-liquid separator may be 0.005% by weight to 0.1% by weight, preferably, 0.01% by weight to 0.07% by weight.

According to one embodiment of the present invention, hydrogen discharged from the upper parts of the first gas-liquid separator and the second gas-liquid separator may be recycled to the reactor. Specifically, hydrogen discharged from the upper part of the first gas-liquid separator through the first decompression step and hydrogen discharged from the upper part of the second gas-liquid separator through the second decompression step are combined into one stream, which is heat-exchanged and compressed and then recycled to the reactor. Alternatively, each stream may be individually heat-exchanged and compressed and then recycled to the reactor. In addition, the hydrogen discharged from the gas-liquid separator may be immediately recycled and mixed with the hydrogen which is supplied to the reactor, and the hydrogen mixture is compressed to a pressure required for the reaction, and then supplied to the reactor, alternatively, the pressure of the discharged hydrogen may be partially increased and mixed with the hydrogen supplied to the reactor, and then the hydrogen mixture is compressed to a pressure required for the reaction, and then supplied to the reactor, alternatively, the discharged hydrogen is immediately compressed to the reaction pressure, and mixed with the hydrogen supplied to the reactor, and the hydrogen mixture may be supplied to the reactor, but is not limited thereto.

In addition, according to one embodiment of the present invention, a step of recycling hydrogen, which is included in the second solution which is discharged from the lower part of the second gas-liquid separator, to the reactor may be further included. For example, hydrogen included in the second solution may be partially evaporated, and the evaporated hydrogen may be recycled to a first hydrogen supply line by compressing through a hydrogen compressor.

The hydrogenation method of the phthalate-based compound of the present invention may gradually recover hydrogen, which is dissolved in the high-pressure reaction product discharged from the reactor, through the two-step decompression as described above, and may improve the stability of facility/operation through the stepwise decompression. In addition, by suppressing the evaporation of hydrogen and liquid products due to rapid decompression, the loss of hydrogen which is a reaction raw material and products may be reduced, thereby increasing the efficiency of the process and economic efficiency.

FIG. 1 illustrates a process apparatus used in the hydrogenation method of the phthalate-based compound of the present invention.

Referring to FIG. 1, the hydrogenation reaction apparatus may consist of a hydrogen compressor (a), a high-pressure pump (c), heat exchangers (b, d), a reactor (e), a first gas-liquid separator (f), a second gas-liquid separator (g), and a heat exchanger (h), etc.

The heat exchanger (b) is a device that heats the gas-phase raw material to prepare the gas-phase raw material at a temperature at which the reaction may proceed, and may be omitted, as needed.

The reactor (e) is a device in which the hydrogenation reaction of the phthalate-based compound included in the liquid-phase raw material and the hydrogen included in the gas-phase raw material occurs, and may further include an external jacket for removing heat in order to control the reaction heat. The gas-phase raw material may be supplied from the upper part or lower part of the reactor, and the liquid-phase raw material may be supplied from the upper part of the reactor.

The first gas-liquid separator (f) and the second gas-liquid separator (g) are devices for separating the target product and hydrogen from the reaction product after the reaction.

The heat exchanger (h) is a device for recycling the separated hydrogen to the reactor by heat exchange.

For example, the hydrogenation method of the phthalate-based compound of the present invention proceeds as follows. The gas-phase raw material (1) and the liquid-phase raw material (3) are compressed through the hydrogen compressor (a) and the high-pressure pump (c), respectively, and each of the compressed raw materials is heated to a temperature suitable for the reaction through the heat exchangers (b, d). The heated gas-phase raw material (2) and liquid-phase raw material (4) are fed together to the reactor (e). In the reactor (e), a reaction between the phthalate-based compound included in the liquid-phase raw material (4) and hydrogen included in the gas-phase raw material (2) occurs. The reaction product (5) generated after the reaction is discharged from the lower part of the reactor, and supplied to the first gas-liquid separator (f) without heat exchange. In the first gas-liquid separator (f), the first hydrogen decompression step is performed, and the gas-phase material (6) including hydrogen is discharged from the upper part of the first gas-liquid separator, and the first solution (7) including the hydrogenated phthalate-based compound is discharged from the lower part thereof. Unreacted hydrogen may be dissolved in the first solution (7) discharged from the lower part of the first gas-liquid separator, and therefore, additional recovery is required, and thus the first solution (7) is injected into the second gas-liquid separator (g). In the second gas-liquid separator, the second hydrogen decompression is performed. The gas-phase material (8) including hydrogen is discharged from the upper part of the second gas-liquid separator, and the second solution (9) including the high-purity hydrogenated phthalate-based compound is discharged from the lower part thereof. The gas-phase material discharged from the upper parts of the first gas-liquid separator (f) and the second gas-liquid separator (g) is cooled through the heat exchanger (h), and then is recycled by supplying to the hydrogen compressor (a) into which the gas-phase raw material is injected.

In FIG. 1, however, the position of each equipment may be changed, and if necessary, other equipment not shown in FIG. 1 may be included, and thus the hydrogenation method of the present invention is not limited to the equipment and process sequence illustrated in FIG. 1.

Effect of the Invention

According to a hydrogenation method of a phthalate-based compound of the present invention, hydrogen is stably separated from a reaction product, and the hydrogen is recycled, and evaporation of a target product is prevented, thereby improving stability and economic efficiency of the process.

BRIEF DESCRIPTION OF DRAWINGS

FIG. 1 is a schematic illustration of an apparatus which is applied to a decompression operation method according to one embodiment of the present invention.

DETAILED DESCRIPTION OF THE EMBODIMENTS

Hereinafter, the actions and effects of the present invention will be explained in more detail through specific exemplary embodiments. However, these exemplary embodiments are no more than illustrations, and the scope of the right of the present invention is not determined thereby.

EXAMPLE

Example 1

As a liquid-phase raw material, a raw material in which dioctyl terephthalate (DOTP) and 2-ethylhexanol (2-EH) were mixed at a weight ratio of 8:2 was injected into a reactor at 9 kg/hr (120° C., 150 barg). Hydrogen was injected at a high pressure into the reactor using a hydrogen compressor such that a molar ratio of DTOP:hydrogen was 1:6 (about 20° ° C. to 40° C., 150 barg). During the hydrogenation reaction, the process was configured using an ASPEN tool at a pressure of 150 barg and a temperature of 150° C.

A reaction product discharged from the hydrogenation reactor was injected into a first gas-liquid separator (about 150° ° C., 150 barg), and an operating pressure of the first gas-liquid separator was set to 150 barg, and a pressure of gas-phase(hydrogen)/liquid-phase discharged from the first gas-liquid separator was set to 20 barg to 25 barg using a control valve.

Thereafter, a first solution discharged from the lower part of the first gas-liquid separator was injected into a second gas-liquid separator. An operating pressure of the second gas-liquid separator was set to 20 barg to 30 barg, and a pressure of a solution discharged from the lower part of the second gas-liquid separator was set to normal pressure (1 barg) using a control valve.

Example 2

The process was configured in the same manner as in Example 1, except that the pressure of the solution discharged from the lower part of the second gas-liquid separator was set to −0.9 barg in Example 1.

Example 3

The process was configured in the same manner as in Example 1, except that hydrogen included in the solution discharged from the lower part of the second gas-liquid separator was recycled after being compressed to 20 barg using a hydrogen compressor in Example 1.

Comparative Example 1

The process was configured in the same manner as in Example 1, except that the second gas-liquid separator was removed, and the pressure of the solution discharged from the lower part of the first gas-liquid separator was set to 0 barg to 5 barg in Example 1.

Comparative Example 2

The process was configured in the same manner as in Comparative Example 1, except that a cooler was installed in front of the first gas-liquid separator, and the reaction product was injected to the first gas-liquid separator through the cooler in Comparative Example 1.

TABLE 1

| | Example 1 | Example 2 | Example 3 | Comparative Example 1 | Comparative Example 2 |
|---|---|---|---|---|---|
| Hydrogen ratio in reaction product (amount of dissolved hydrogen/ total input amount of hydrogen) | 9.8% | 9.8% | 9.8% | 9.8% | 9.8% |
| Hydrogen recovery rate [1)] | 77% | 90% | 97% | 0.0% | 0.0% |
| Hydrogen discharge concentration [2)] | 0.032% | 0.011% | 0.004% | 0.140% | 0.140% |

[1)] Hydrogen recovery rate = (Amount of hydrogen discharged from upper part of gas-liquid separator/Amount of dissolved hydrogen in reaction product) * 100
[2)] Example; Concentration of hydrogen in solution discharged from lower part of second gas-liquid separator (wt %), Comparative Example; Concentration of hydrogen in solution discharged from lower part of first gas-liquid separator (wt %).

Referring to Table 1, the hydrogenation method of the phthalate compound of Example was able to stably recover about 70% or more of the dissolved hydrogen in the reaction product through a two-stage decompression step, and the final concentration of hydrogen discharged from the lower part of the gas-liquid separator was reduced. In contrast, Comparative Example, in which a single-stage gas-liquid separator was configured, could not recover hydrogen in the gas phase, and it was confirmed that the concentration of hydrogen discharged from the lower part was higher than that of Example. Accordingly, it was confirmed that the hydrogenation method of the phthalate compound of the present invention has high process stability and the increased hydrogen recovery rate.

REFERENCE NUMERALS a: Hydrogen compressor
b: Heat exchanger
c: High-pressure pump
d: Heat exchanger
c: Reactor
f: First gas-liquid separator
g: Second gas-liquid separator
h: Heat exchanger
1, 11, 2: Gas-phase raw material
3, 33, 4: Liquid-phase raw material
5: Reaction product
6, 8, 10: Gas-phase material
7: First solution
9: Second solution

The invention claimed is:

1. A hydrogenation method of a phthalate-based compound, the method comprising:
- the step of injecting, into a reactor, a gas-phase raw material including hydrogen and a liquid-phase raw material including the phthalate-based compound;
- the step of performing a hydrogenation reaction of the gas-phase raw material and the liquid-phase raw material in the presence of a catalyst in the reactor;
- a first decompression step of separating and decompressing, in a first gas-liquid separator, a first solution and the gas-phase material containing hydrogen from the reaction product after the reaction step; and
- a second decompression step of separating and decompressing, in a second gas-liquid separator, a second solution and the gas-phase material containing hydrogen from the first solution discharged from the lower part of the first gas-liquid separator,
- wherein an operating pressure of the first gas-liquid separator is 100 barg to 200 barg,
- wherein a pressure of the gas-phase material discharged from the upper part of the first gas-liquid separator is 5 barg to 50 barg,
- wherein an operating pressure of the second gas-liquid separator is 5 barg to 100 barg,
- wherein a pressure of the gas-phase material discharged from the upper part of the second gas-liquid separator is 5 barg to 50 barg,
- wherein a pressure of the second solution discharged from the lower part of the second gas-liquid separator is-1 barg to 25 barg,
- wherein a concentration of hydrogen in the second solution discharged from the lower part of the second gas-liquid separator is 0.005% by weight to 0.1% by weight.

2. The method of claim 1, wherein the liquid-phase raw material further includes alcohol or a hydrogenated phthalate-based compound.

3. The method of claim 1, wherein a pressure of hydrogen supplied to the reactor is 100 barg to 200 barg.

4. The method of claim 1, wherein an operating temperature of the reactor is 100° C. to 300° C., and an operating pressure thereof is 100 barg to 200 barg.

5. The method of claim 1, wherein the active ingredient of the catalyst is included in an amount of 0.3 parts by weight to 5 parts by weight with respect to 100 parts by weight of a carrier.

6. The method of claim 1, wherein the reaction product discharged from the reactor is directly connected to the first gas-liquid separator.

7. The method of claim 1, further comprising the step of recycling hydrogen, which is discharged from the upper parts of the first gas-liquid separator and the second gas-liquid separator, to reactor.

8. The method of claim 1, further comprising the step of recycling hydrogen, which is included in the second solution discharged from the lower part of the second gas-liquid separator, to reactor.

* * * * *